US012741929B2

(12) United States Patent
Ciufolini et al.

(10) Patent No.: US 12,741,929 B2
(45) **Date of Patent: *Sep. 22, 2026**

(54) MC3-TYPE LIPIDS

(71) Applicant: NanoVation Therapeutics Inc., Vancouver (CA)

(72) Inventors: Marco A. Ciufolini, Vancouver (CA); Fariba Saadati, Vancouver (CA); Anthony C. Y. Tam, Vancouver (CA); Daniel Kurek, Vancouver (CA); Dominik Witzigmann, Binzen (DE); Jayesh Kulkarni, Vancouver (CA)

(73) Assignee: NanoVation Therapeutics Inc., Vancouver (CA)

( * ) Notice: Subject to any disclaimer, the term of this patent is extended or adjusted under 35 U.S.C. 154(b) by 266 days.

This patent is subject to a terminal disclaimer.

(21) Appl. No.: 18/564,754

(22) PCT Filed: May 26, 2022

(86) PCT No.: PCT/CA2022/050856

§ 371 (c)(1),
(2) Date: Nov. 28, 2023

(87) PCT Pub. No.: WO2022/246571

PCT Pub. Date: Dec. 1, 2022

(65) Prior Publication Data

US 2024/0383843 A1 Nov. 21, 2024

Related U.S. Application Data

(60) Provisional application No. 63/214,995, filed on Jun. 25, 2021, provisional application No. 63/194,471, filed on May 28, 2021.

(51) Int. Cl.
*C07C 229/12* (2006.01)
*A61K 9/1272* (2025.01)

(52) U.S. Cl.
CPC .......... *C07C 229/12* (2013.01); *A61K 9/1272* (2013.01)

(58) Field of Classification Search
None
See application file for complete search history.

(56) References Cited

U.S. PATENT DOCUMENTS 6,861,551 B2 3/2005 Tanabe et al.
8,058,069 B2 11/2011 Yaworski et al.
(Continued)

FOREIGN PATENT DOCUMENTS

CN 112299951 A 2/2021
EP 3020701 B1 * 9/2018 .............. A61P 35/00
(Continued)

OTHER PUBLICATIONS

Muthusamy Jayaraman et al. "Maximizing the Potency of siRNA Lipid Nanoparticles for Hepatic Gene Silencing In Vivo." Angewandte Chemie International Edition, vol. 51, 2012, pp. 8529-8533 and 126 pages of supplemental information. (Year: 2012).*
(Continued)

*Primary Examiner* — Isaac Shomer
(74) *Attorney, Agent, or Firm* — Lamson IP

(57) ABSTRACT

Provided is lipid and methods of making such lipid, the lipid having the structure of:

Formula A

A (Continued)

each R is independently an alkyl of $C_{12}$ to $C_{16}$, each alkyl having 1 to 3 C=C double bonds, wherein at least one of the double bonds is of Z geometry;

R' is an optional alkyl;

W is O, NH or NR", wherein R" is a $C_1$ to $C_3$ alkyl group, such as a methyl;

X is either absent or present, and if present, X is O, NH, or the NR"; and

Z is an alkylamino chain as defined by $[-(CH_2)_m-NG^1G^2G^3]$, wherein m is 1-5 and $G^1$ and $G^2$ are, independently, the $C_1$ to $C_3$ alkyl group, $G^3$ is absent, a hydrogen or the $C_1$ to $C_3$ alkyl group.

11 Claims, 3 Drawing Sheets

(56) References Cited

U.S. PATENT DOCUMENTS 8,158,601 B2 4/2012 Chen et al.
9,018,187 B2 4/2015 Heyes et al.
9,061,063 B2 6/2015 Maier et al.
9,139,554 B2 9/2015 Hope et al.
9,394,234 B2 7/2016 Chen et al.
9,682,922 B2 6/2017 Manoharan et al.
10,266,484 B2 4/2019 Manoharan et al.
10,533,176 B2 1/2020 Koizumi et al.
12,121,591 B2 * 10/2024 Arnold ............... A61K 47/6929
2006/0135819 A1 6/2006 Tanabe et al.
2010/0324120 A1 * 12/2010 Chen .................... A61K 31/713 514/777
2012/0095075 A1 4/2012 Manoharan et al.
2013/0072543 A1 3/2013 Bennett et al.
2020/0345641 A1 * 11/2020 De Koker .............. A61K 9/127
2024/0116862 A1 4/2024 Ciufolini et al.

FOREIGN PATENT DOCUMENTS

WO 2009132131 A1 10/2009
WO 2010042877 A1 4/2010
WO 2010048536 A2 4/2010
WO 2010054401 A1 5/2010
WO 2010088537 A2 8/2010
WO 2010144740 A1 12/2010
WO 2011141705 A1 11/2011
WO 2013086322 A1 6/2013
WO 2014018578 A1 1/2014
WO 2023147657 A1 8/2023

OTHER PUBLICATIONS

Pieter R. Cullis and Michael J. Hope. "Lipid Nanoparticle Systems for Enabling Gene Therapies." Molecular Therapy, vol. 25, No. 7, Jul. 2017, pp. 1467-1475. (Year: 2017).*

Linde Schoenmaker et al. "mRNA-lipid nanoparticle COVID-19 vaccines: Structure and stability." International Journal of Pharmaceutics, vol. 601, 2021, Article 120586, pp. 1-13, published Apr. 9, 2021. (Year: 2021).*

Clement, Rene, "On a Method for the Preparation of 1,19-nonadecanedioic acid", 1962, 254:2794-2795.

Hashiba et al., Branching Ionizable Lipids Can Enhance the Stability, Fusogenicity, and FunctionalSmall Science, 2022, 3(1):2200071.

International Preliminary Report on Patentability for PCT/CA2022/050835, Jul. 17, 2023.

International Preliminary Report on Patentability for PCT/CA2022/050853, Jun. 30, 2023.

International Preliminary Report on Patentability for PCT/CA2022/050856, Sep. 14, 2023.

International Search Report and Written Opinion for PCT/CA2022/050835, Aug. 29, 2022.

International Search Report and Written Opinion for PCT/CA2022/050853, Aug. 26, 2022.

International Search Report and Written Opinion for PCT/CA2022/050856, Aug. 29, 2022.

International Search Report and Written Opinion for PCT/CA2023/050129, Apr. 14, 2023.

Jayaraman et al., "Maximizing the Potency of siRNA Lipid Nanoparticles for Hepatic Gene Silencing In Vivo", Angewandte Chemie, 2012, 51:8529-8533.

Kulkarni et al., "Design of lipid nanoparticles for in vitro and in vivo delivery of plasmid DNA", Nanomedicine: Nanotechnology, Biology, and Medicine, 2017, 13:1377-1387.

Second Written Opinion for PCT/CA2022/050835, Apr. 11, 2023.

Second Written Opinion for PCT/CA2022/050853, Apr. 5, 2023.

Semple et al., "Rational design of cationic lipids for siRNA delivery", Nature Biotechnology, 2010, 28(2): 172-178.

Tanabe et al., "Dichloro-bis(trifluoromethanesulfonato)titanium(IV) as an Effective Promoter in the Claisen Ester Condensation", Chemistry Letters, The Chemical Society of Japan, 1984, 1867-1970.

Yoshida et al., "TICI4/Bu3N/catalytic TMSOTf: Efficient Agent for Direct Aldol Addition and Claisen Condensation", Tetrahedron Letters, 1997, 50:8727-8730.

* cited by examiner

MC3-TYPE LIPIDS

CROSS-REFERENCE TO RELATED APPLICATIONS

This application is a national stage application of PCT/CA2022/050856 having an international filing date of May 26, 2022, which claims the priority benefit of U.S. provisional patent application No. 63/194,471 filed on May 28, 2021 and U.S. provisional patent application No. 63/214,995 filed on Jun. 25, 2021, which are each incorporated herein by reference in their entirety.

TECHNICAL FIELD

Provided herein are lipids that may be formulated in a delivery vehicle so as to facilitate the encapsulation of a wide range of therapeutic agents or prodrugs therein, such as, without limitation, nucleic acids (e.g., RNA or DNA), proteins, peptides, pharmaceutical drugs and salts thereof.

BACKGROUND

Nucleic acid-based therapeutics have enormous potential in medicine. To realize this potential, however, the nucleic acid must be delivered to a target site in a patient. This presents challenges since nucleic acid is rapidly degraded by enzymes in the plasma upon administration. Even if the nucleic acid is delivered to a disease site, there still remains the challenge of intracellular delivery. To address these problems, lipid nanoparticles have been developed that protect nucleic acid from such degradation and facilitate delivery across cellular membranes to gain access to the intracellular compartment, where the relevant translation machinery resides.

A key component of lipid nanoparticles (LNPs) is an ionizable lipid. The ionizable lipid is typically positively charged at low pH, which facilitates association with the negatively charged nucleic acid. However, the ionizable lipid is neutral at physiological pH, making it more biocompatible in biological systems. Further, it has been suggested that after the lipid nanoparticles are taken up by a cell by endocytosis, the ability of these lipids to ionize at low pH enables endosomal escape. This in turn enables the nucleic acid to be released into the intracellular compartment. While most research on cationic LNPs has focused on the formulation of nucleic acid, the delivery of other therapeutic agents or prodrugs besides nucleic acid is possible as well using the delivery platform.

Significant research has been devoted to identifying amino lipids with high potency. An ionizable lipid, referred to as DLin-MC3-DMA or "MC3" (dilinoleyl-methyl-4-dimethylaminobutyrate), constitutes the state-of-the-art ionizable lipid for siRNA formulations. This ionizable lipid is a key component of Onpattro®, a lipid nanoparticle formulation incorporating siRNA that silences genes causing a genetic neurodegenerative disease referred to as hereditary transthyretin-mediated amyloidosis. Such formulations containing MC3 constituted the first small interfering RNA (siRNA) based treatments to be approved by the U.S. Food and Drug Administration (FDA).

The MC3 ionizable lipid is widely regarded as being an improved version of another amino lipid referred to as KC2, being about 3 times more efficacious. In a study of over 50 amino lipids, MC3 was identified as having an $ED_{50}$ or 0.03 while that of KC2 was 0.10 for FVII gene silencing in mice using siRNA. (Jayaraman et al., 2012, Angew. Chem. Int. Ed., 51:8529-8533). This means that formulations containing MC3 require about 3 times less siRNA to attain the same end-result as similar formulations based on KC2. Since nucleic acid is costly, this translates into considerable savings for large scale manufacture of the ionizable lipid.

Both MC3 and KC2 amino lipids (structures below) have two carbon chains (denoted as "R" herein) converging onto a single carbon atom, which in turn serves as the anchoring point for an ionizable terminal "head" group.

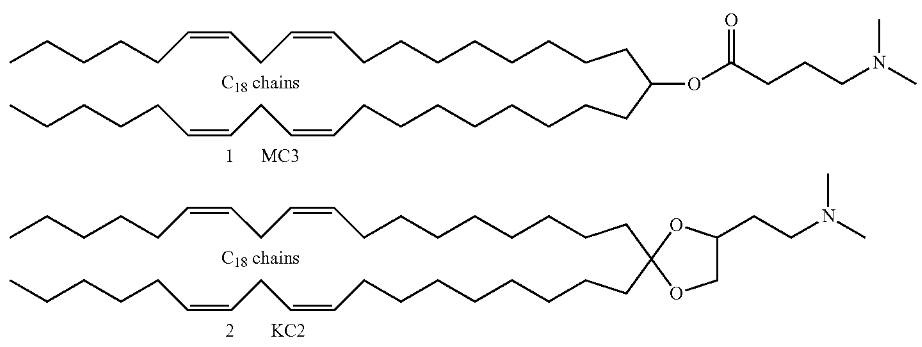

1 MC3

2 KC2

In both MC3 and KC2, the carbon chains are unsaturated $C_{18}$ moieties derived from linoleic acid or a corresponding ester. These 18 carbon unsaturated chains are the best chains yet identified for maximum efficacy of siRNA formulations. (Semple et al., 2010, Nat. Biotechnol. 28:172-176 and Heyes et al., 2005, J. Controlled Release, 107:276-287). Further, amino lipids with chains shorter than 18 carbon atoms are difficult to prepare using conventional synthetic routes. While shorter-chain lipids could be produced from esters of unsaturated fatty acids incorporating fewer than 18 C atoms, such esters are either not found in nature, or are extremely costly to synthesize using known methods. Accordingly, little attention has been devoted to examining amino lipids for nucleic acid delivery having unsaturated chains of fewer than 18 carbon atoms.

There is a need in the art for ionizable lipids for delivery of therapeutic agents or prodrugs that have a potency that is improved or comparable to known lipids and that can be manufactured conveniently and cost effectively.

Definitions

As used herein, a "MC3-type lipid" refers to any lipid, including but not limited to an ionizable lipid, having a structure as defined by Formula A herein or equivalents thereof.

As used herein, the term "ionizable lipid" refers to a lipid that, at a given pH, is in an electrostatically neutral form and that may either accept or donate protons, thereby becoming electrostatically charged, and for which the electrostatically neutral form has a calculated logarithm of the partition coefficient between water and 1-octanol (i.e., a c Log P) greater than 8. As used herein, the term "alkyl" with reference to an R group as described herein is a carbon-containing chain that is linear or branched and that has varying degrees of unsaturation.

As used herein, the term "$C_1$ to $C_3$ alkyl" refers to a linear or branched carbon chain having a total of up to 3 carbon atoms, optionally unsaturated.

As used herein, the term "helper lipid" means a compound selected from: a sterol such as cholesterol or a derivative thereof; a diacylglycerol or a derivative thereof, such as a glycerophospholipid, including phosphatidic acid (phosphatidate) (PA), phosphatidylethanolamine (cephalin) (PE), phosphatidylcholine (PC), phosphatidylserine (PS), and the like; and a sphingolipid, such as a ceramide, a sphingomyelin, a cerebroside, a ganglioside, or reduced analogues thereof, that lack a double bond in the sphingosine unit. The term encompasses lipids that are either naturally-occurring or synthetic.

As used herein, the term "delivery vehicle" includes any preparation in which the lipid described herein is capable of being formulated and includes but is not limited to delivery vehicles comprising helper lipids.

As used herein, the term "nanoparticle" is any suitable particle in which the lipid can be formulated and that may comprise one or more helper lipid components. The one or more lipid components may include an ionizable lipid prepared by the method described herein and/or may include additional lipid components, such as a helper lipid. The term includes, but is not limited to, vesicles with one or more bilayers, including multilamellar vesicles, unilamellar vesicles and vesicles with an electron-dense core. The term also includes polymer-lipid hybrids, including particles in which the lipid is attached to a polymer.

As used herein, the term "encapsulation," with reference to incorporating a cargo molecule within a delivery vehicle refers to any association of the cargo with any component or compartment of the delivery vehicle such as a nanoparticle.

SUMMARY

The disclosure seeks to address one or more limitations of known art or to provide useful alternatives thereof.

The present disclosure is based, at least in part, on the surprising discovery that certain MC3-type amino lipids having unsaturated chains with less than 18 carbon atoms have enhanced nucleic acid delivery efficacy when formulated in a delivery vehicle. The potency of such short-chain amino lipids is better or comparable to that of the state-of-the-art amino lipid, MC3 having dilinoleyl chain (unsaturated $C_{18}$). For example, the inventors have found that a short-chain MC3-type lipid (e.g., having unsaturated $C_{17}$ moieties) has an mRNA efficacy in vitro and in vivo when formulated in a delivery vehicle that is superior or comparable to that of the longer chain, benchmark lipid MC3. The inventors have further found that siRNA-containing delivery vehicles including short-chain MC3-type lipids (e.g., having unsaturated $C_{17}$ moieties) have comparable or even slightly better potency in some instances than MC3, which is contrary to studies showing that the dilinoleyl chain (unsaturated $C_{18}$) of the MC3 lipid is considered optimal for activity.

Further, the inventors have identified a class of short chain (less than $C_{18}$ unsaturated moieties), MC3-type lipids that are easily prepared by a method described herein in which longer chain fatty acid esters (e.g., commercially available unsaturated $C_{18}$ to $C_{22}$) are shortened and subsequently converted to the MC3-type lipids in a synthesis route including a Claisen condensation step as described herein. Thus, the present disclosure further addresses previous shortcomings with synthesizing MC3-type lipids having less than 18 carbon atoms and allows for the preparation of a new class of short-chain lipids.

Other objects, features, and advantages of the present disclosure will be apparent to those of skill in the art from the following detailed description and figures.

DETAILED DESCRIPTION

MC3-Type Lipids

Figure 1A:
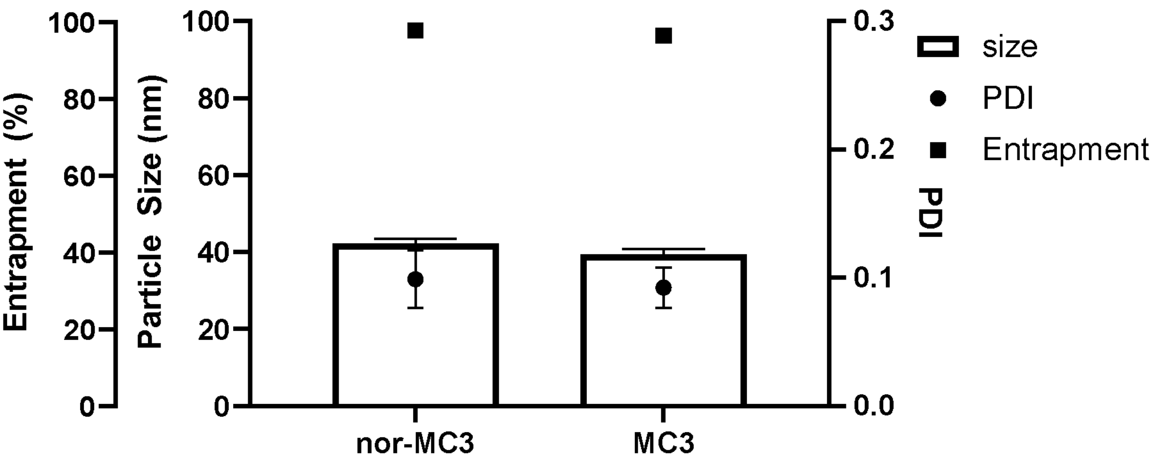
FIG. 1A is a bar graph showing entrapment (%), particle size and polydispersity index (PDI) of mRNA-containing lipid nanoparticles (LNPs) comprising the ionizable lipid nor-MC3 or DLin-MC3-DMA (MC3). The LNPs are composed of 50/10/38.5/1.5 mol % of ionizable lipid/DSPC/chol/PEG-DMG and the amine-to-phosphate (N/P) was 6.

The present disclosure provides an MC3-type lipid having the structure of Formula A:

Formula A

A

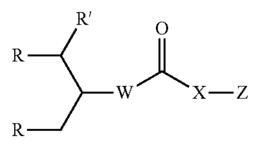

each R is independently an alkyl group having a carbon backbone of $C_{12}$ to $C_{16}$, each alkyl group having 1 to 3 C═C double bonds, or 1 to 2 double bonds or 2 double bonds, wherein at least one of the double bonds is of Z geometry, and most advantageously each double bond of R is of Z geometry;

R' is an optional alkyl group having a backbone of $C_2$ to $C_{24}$ and having 0 to 3 C=C double bonds;

each R, and the R' alkyl group if present, is optionally substituted at one or more positions with a $C_1$ to $C_3$ alkyl group;

W is O, NH or NR", wherein R" is the $C_1$ to $C_3$ alkyl, such as a methyl;

X is either absent or present, and if present is O, NH, or NR", wherein R" is the $C_1$ to $C_3$ alkyl, such as a methyl;

Z is an alkylamino chain as defined by $[-(CH_2)_m-NG^1G^2G^3]$, wherein m is 1 to 5, 2 to 4 or 2 to 3 and $G^1$ and $G^2$ are, independently, the $C_1$ to $C_3$ alkyl, such as a methyl, $G^3$ is absent (i.e., it is a lone pair), a hydrogen or the $C_1$ to $C_3$ alkyl, such as a methyl.

In one embodiment, each R alkyl group has two double bonds of Z geometry.

In one embodiment, the $C_1$ to $C_3$ alkyl group of Formula A substituted on the R, the R' alkyl backbone or R" of NR" is selected from methyl, ethyl, propyl, isopropyl, butyl, isobutyl and tert-butyl. The $C_1$ to $C_3$ alkyl group, if present, typically replaces a hydrogen atom on the R and/or R' carbon backbone.

In another embodiment, the lipid of Formula A has the structure of Formula B below.

Formula B

B

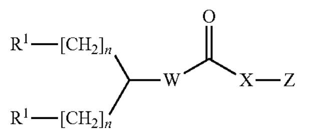

wherein the R alkyl group (see Formula A) is represented by an $R^1-[CH_2]_n$ moiety, which is a linear alkyl group that is $C_{12}$ to $C_{17}$, wherein the n of the $[CH_2]_n$ moiety is 2-7, wherein each $R^1$ is $C_{15}$ or less and the $R^1-[CH_2]_n$ moiety is optionally substituted with the $C_1$ to $C_3$ alkyl group; and wherein each $R^1$ independently has 1 to 3 double bonds, or 1 to 2 double bonds or 2 double bonds, wherein at least one of the double bonds is of Z geometry, most advantageously each double bond of $R^1$ is of Z geometry.

In another embodiment, the X of Formula B is absent and the lipid has the structure of Formula C as set out below.

Formula C

C

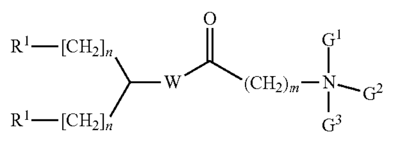

wherein m is 1 to 5, 2 to 4 or 2 to 3;

$G^1$ and $G^2$ are, independently, the $C_1$ to $C_3$ alkyl group, most advantageously each $G^1$ and $G^2$ is a methyl group; and $G^3$ is absent (i.e., it is a lone pair) or a hydrogen (as dependent on pH).

In another embodiment, the lipid of Formula B has the structure of Formula D set forth below.

Formula D

D

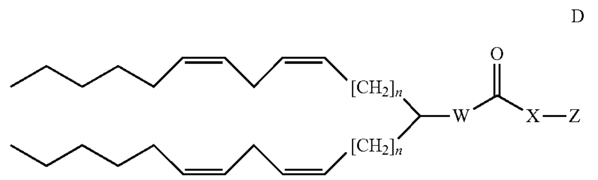

wherein n is 2 to 7.

In another non-limiting example, the lipid of general Formula B above has the structure of Formula E provided below.

Formula E

E

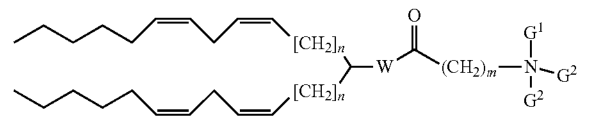

wherein n is 2 to 7.

In yet a further embodiment, the lipid of Formula B has the structure of Formula F below:

Formula F

F

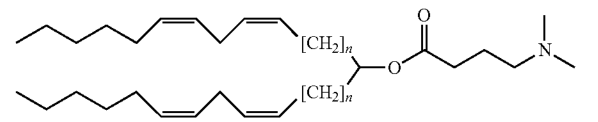

In another embodiment, the lipid has the structure of nor-MC3:

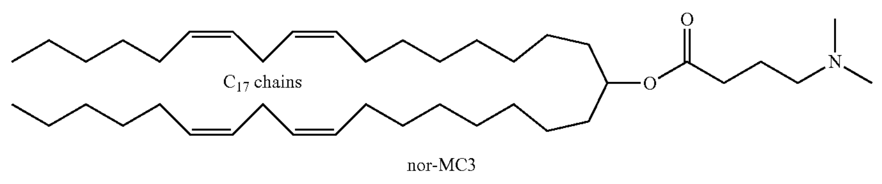 [SMILES: CCCCC/C=C\C/C=C\CCCCCCCC(CCCCCCC/C=C\C/C=C\CCCCC)OC(=O)CCCN(C)C]

nor-MC3

Methods to Produce MC3-Type Lipids Having $C_{17}$ or Shorter R Alkyl Groups

MC3-type lipids having $C_{17}$ or shorter R alkyl groups can be prepared using the methods described below. While a linoleate ester (e.g., methyl linoleate) is the starting material in the synthetic schemes described below, as would be appreciated by those of skill in the art, other fatty acids could serve as the starting material and the schemes set forth below are merely illustrative of select embodiments.

As previously noted, in both KC2 and MC3 ionizable amino lipids, the carbon chains are unsaturated $C_{18}$ moieties derived from linoleic acid or a corresponding ester.

Scheme 1

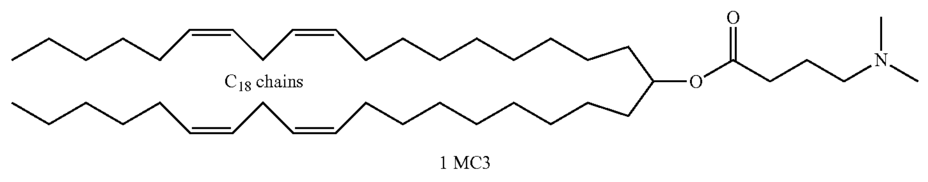

1 MC3

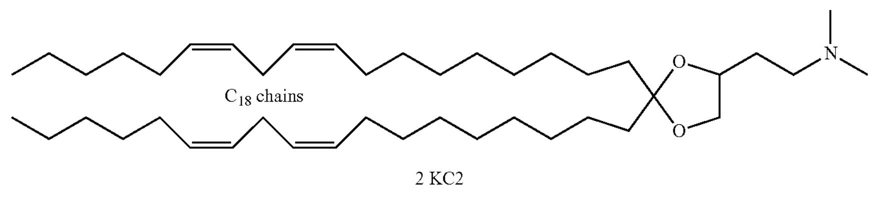

2 KC2

MC3 1 and analogues thereof may be represented by general formula 3 (Scheme 2 below). The methods described herein provide for the synthesis of MC3-type lipids 4, wherein the chains incorporate 17 carbon atoms or less:

Scheme 2

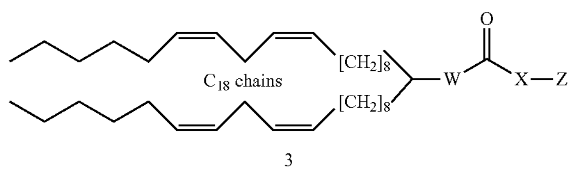

3

-continued

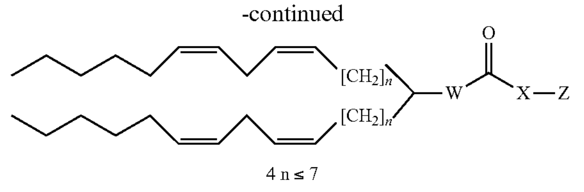

4 n ≤ 7 wherein n is 2-7;

W is O, NH or NR", wherein R" is a $C_1$ to $C_3$ alkyl, such as a methyl;

X is either absent or present, and if present is O, NH, or NR", wherein R" is the $C_1$ to $C_3$ alkyl, such as the methyl; and Z is an alkylamino chain as defined by [—$(CH_2)_m$—$NG^1G^2G^3$], wherein m is 1 to 5, 2 to 4 or 2 to 3 and $G^1$ and $G^2$ are, independently, the $C_1$ to $C_3$ alkyl group, such as a methyl, $G^3$ is absent (i.e., it is a lone pair), a hydrogen or a $C_1$ to $C_3$ alkyl, such as a methyl.

Lipids of the type 4 wherein n=7 are described in co-pending and co-owned U.S. Provisional Application No. 63/194,471 titled "Method for Producing an Ionizable Lipid", which is incorporated herein by reference.

U.S. Provisional Application No. 63/194,471 also describes methods to make ionizable lipids from a generic fatty acid ester 5 (Scheme 3). As described therein, the fatty acid ester is subjected to Claisen condensation under Mukaiyama conditions, resulting in ketoester 6, which may optionally undergo addition of an $R^2$ alkyl group.

Scheme 3

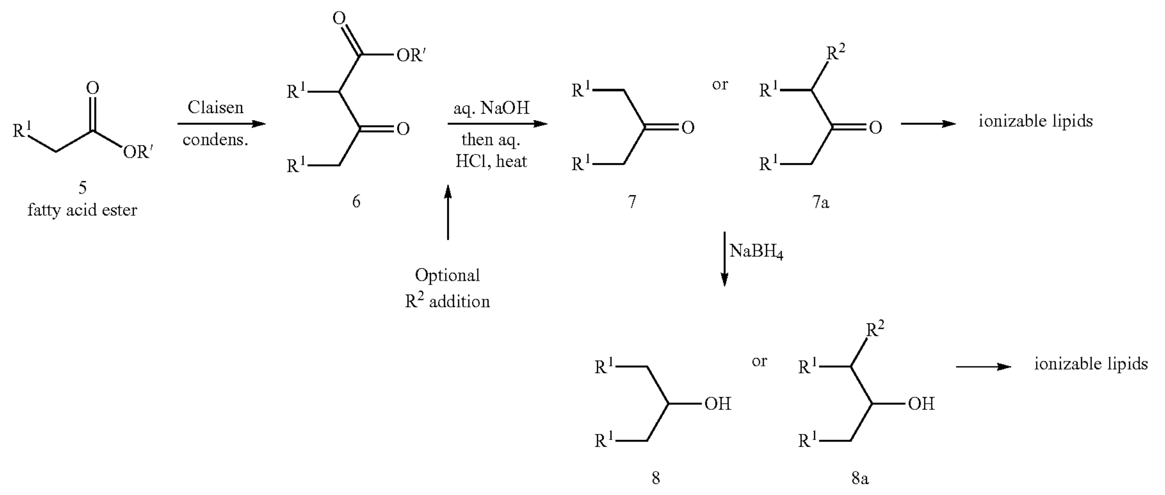

5
fatty acid ester

6

7 or 7a 8 or 8a

The ketoester is subsequently hydrolyzed and decarboxylated to provide ketones 7 (or 7a), which may be further reduced to alcohols 8 (or 8a). Ketalization of ketones 7 yields KC2-type lipids and esterification of alcohols 8 yields MC3-type lipids as set forth in co-owned and co-pending U.S. Provisional Application No. 63/194,471.

The chemistry is such that an ester incorporating n carbon atoms in its acid portion will provide ionizable lipids with hydrophobic chains having n−1 C atoms. For example, methyl linoleate, a $C_{18}$ fatty acid ester, yields nor-MC3 displaying $C_{17}$ chains (Scheme 4). The structures of such nor-lipid can be represented as structure 4 above, in which n=7.

Scheme 4

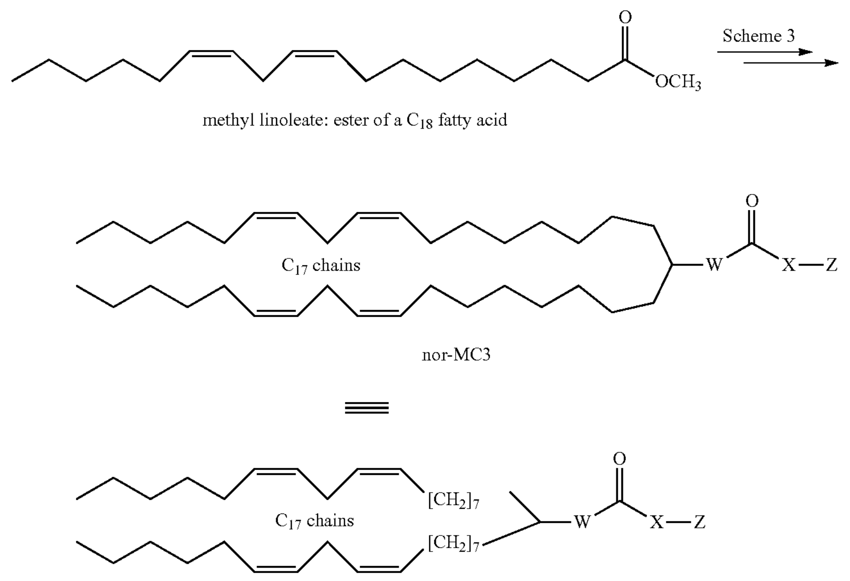

methyl linoleate: ester of a $C_{18}$ fatty acid nor-MC3

Shorter-chain lipids of the type 4 would be available from esters of unsaturated fatty acids incorporating fewer than 18 carbon atoms.

Formulation of the Lipid in a Delivery Vehicle

The MC3-type lipid of the disclosure may be formulated in a variety of drug delivery vehicles (also referred to herein as a "delivery vehicle") known to those of ordinary skill in the art. An example of a delivery vehicle is a lipid nanoparticle, which includes liposomes, lipoplexes, polymer nanoparticles comprising lipids, polymer-based nanoparticles, emulsions, and micelles.

In one embodiment, the MC3-type lipid of the disclosure is formulated in a delivery vehicle by mixing them with additional lipids, including helper lipids, such as vesicle forming lipids and optionally an aggregation inhibiting lipid, such as a hydrophilic polymer-lipid conjugate (e.g., PEG-lipid).

As set forth previously, a helper lipid includes a sterol, a diacylglycerol, a ceramide or derivatives thereof.

Examples of sterols include cholesterol, or a cholesterol derivative, such as cholestanol, cholestanone, cholestenone, coprostanol, cholesteryl-2'-hydroxyethyl ether, cholesteryl-4'-hydroxybutyl ether, beta-sitosterol, fucosterol, and the like.

Examples of diacylglycerols include dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain embodiments, the phospholipid is DPPC, DSPC, or mixtures thereof. These lipids may be synthesized or obtained from natural sources, such as from egg.

A suitable ceramide derivative is egg sphingomyelin or dihydrosphingomyelin.

Delivery vehicles incorporating the MC3-type lipids of the disclosure can be prepared using a wide variety of well described formulation methodologies known to those of skill in the art, including but not limited to extrusion, ethanol injection and in-line mixing. In one embodiment, the preparation method is an in-line mixing technique in which aqueous and organic solutions are mixed using a rapid-mixing device as described in Kulkarni et al., 2018, ACS Nano, 12:4787 and Kulkarni et al., 2017, Nanoscale, 36:133347, each of which is incorporated herein by reference in its entirety.

The delivery vehicle can also be a nanoparticle that is a lipoplex that comprises a lipid core stabilized by a surfactant. Vesicle-forming lipids may be utilized as stabilizers. The lipid nanoparticle in another embodiment is a polymer-lipid hybrid system that comprises a polymer nanoparticle core surrounded by stabilizing lipid.

Nanoparticles comprising the MC3-type lipid of the disclosure may alternatively be prepared from polymers without lipids. Such nanoparticles may comprise a concentrated core of a therapeutic agent that is surrounded by a polymeric shell or may have a solid or a liquid dispersed throughout a polymer matrix.

The MC3-type lipids described herein can also be incorporated into emulsions, which are drug delivery vehicles that contain oil droplets or an oil core. An emulsion can be lipid-stabilized. For example, an emulsion may comprise an oil filled core stabilized by an emulsifying component such as a monolayer or bilayer of lipids.

The MC3-type lipid may be incorporated into a micelle. Micelles are self-assembling particles composed of amphipathic lipids or polymeric components that are utilized for the delivery of agents present in the hydrophobic core.

A further class of drug delivery vehicles known to those of skill in the art that can be used to formulate the MC3-type lipid herein is a carbon nanotube.

Delivery of Nucleic Acid, Genetic Material, Proteins, Peptides or Other Charged Agents The MC3-type lipid disclosed herein may facilitate the incorporation of a compound or molecule (referred to herein also as "cargo" or "cargo molecule") bearing a net negative or positive charge into the delivery vehicle and subsequent delivery to a target cell in vitro or in vivo.

In one embodiment, the cargo molecule is genetic material, such as a nucleic acid. The nucleic acid includes, without limitation, RNA, including small interfering RNA (siRNA), small nuclear RNA (snRNA), micro RNA (miRNA), messenger RNA (mRNA) or DNA such as vector DNA or linear DNA. The nucleic acid length can vary and can include nucleic acid of 5-50,000 nucleotides in length. The nucleic acid can be in any form, including single stranded DNA or RNA, double stranded DNA or RNA, or hybrids thereof. Single stranded nucleic acid includes antisense oligonucleotides.

In one embodiment, the cargo is an mRNA, which includes a polynucleotide that encodes at least one peptide, polypeptide or protein. The mRNA includes, but is not limited to, small activating RNA (saRNA) and trans-amplifying RNA (taRNA), as described in co-pending U.S. provisional Application No. 63/195,269, titled "mRNA Delivery Using Lipid Nanoparticles", which is incorporated herein by reference.

The mRNA as used herein encompasses both modified and unmodified mRNA. In one embodiment, the mRNA comprises one or more coding and non-coding regions. The mRNA can be purified from natural sources, produced using recombinant expression systems and optionally purified, or may be chemically synthesized.

In those embodiments in which an mRNA is a chemically synthesized molecule, the mRNA can comprise nucleoside analogs such as analogs having chemically modified bases or sugars, and/or backbone modifications. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The mRNAs of the disclosure may be synthesized according to any of a variety of known methods. For example, mRNAs in certain embodiments may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor.

In some embodiments, in vitro synthesized mRNA may be purified before encapsulation to remove undesirable impurities including various enzymes and other reagents used during mRNA synthesis.

The present disclosure may be used to encapsulate mRNAs of a variety of lengths. In some embodiments, the present disclosure may be used to encapsulate in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

While mRNA provided from in vitro transcription reactions may be desirable in certain embodiments, other sources of mRNA are contemplated, such as mRNA produced from bacteria, fungi, plants, and/or animals.

The mRNA sequence may comprise a reporter gene sequence, although the inclusion of a reporter gene sequence in pharmaceutical formulations for administration is optional. Such sequences may be incorporated into mRNA for in vitro studies or for in vivo studies in animal models to assess biodistribution.

In another embodiment, the cargo is an siRNA. An siRNA becomes incorporated into endogenous cellular machineries to result in mRNA breakdown, thereby preventing transcription. Since RNA is easily degraded, its incorporation into a delivery vehicle can reduce or prevent such degradation, thereby facilitating delivery to a target site.

The siRNA encompassed by embodiments of the disclosure may be used to specifically inhibit expression of a wide variety of target polynucleotides. The siRNA molecules targeting specific polynucleotides may be readily prepared according to procedures known in the art. An siRNA target site may be selected and corresponding siRNAs may be chemically synthesized, created by in vitro transcription, or expressed from a vector or PCR product. A wide variety of different siRNA molecules may be used to target a specific gene or transcript. The siRNA may be double-stranded RNA, or a hybrid molecule comprising both RNA and DNA, e.g., one RNA strand and one DNA strand. The siRNA may be of a variety of lengths, such as 15 to 30 nucleotides in length or 20 to 25 nucleotides in length. In certain embodiments, the siRNA is double-stranded and has 3' overhangs or 5' overhangs. In certain embodiments, the overhangs are UU or dTdT 3'. In particular embodiments, the siRNA comprises a stem loop structure.

In a further embodiment, the cargo molecule is a microRNA or small nuclear RNA. Micro RNAs (miRNAs) are short, noncoding RNA molecules that are transcribed from genomic DNA, but are not translated into protein. These RNA molecules are believed to play a role in regulation of gene expression by binding to regions of target mRNA. Binding of miRNA to target mRNA may down-regulate gene expression, such as by inducing translational repression, deadenylation or degradation of target mRNA. Small nuclear RNA (snRNA) are typically longer noncoding RNA molecules that are involved in gene splicing. The snRNA molecules may have therapeutic importance in diseases that are an outcome of splicing defects.

In another embodiment, the cargo is a DNA vector as described in co-owned and co-pending U.S. Application No. 63/202,210 titled "DNA Vector Delivery Using Lipid Nanoparticles", which is incorporated herein by reference. The DNA vectors may be administered to a subject for the purpose of repairing, enhancing or blocking or reducing the expression of a cellular protein or peptide. Accordingly, the nucleotide polymers can be nucleotide sequences including genomic DNA, cDNA, or RNA.

As will be appreciated by those of skill in the art, the vectors may encode promoter regions, operator regions or structural regions. The DNA vectors may contain double-stranded DNA or may be composed of a DNA-RNA hybrid. Non-limiting examples of double-stranded DNA include structural genes, genes including operator control and termination regions, and self-replicating systems such as vector DNA.

Single-stranded nucleic acids include antisense oligonucleotides (complementary to DNA and RNA), ribozymes and triplex-forming oligonucleotides. In order to have prolonged activity, the single-stranded nucleic acids will preferably have some or all of the nucleotide linkages substituted with stable, non-phosphodiester linkages, including, for example, phosphorothioate, phosphorodithioate, phosphoroselenate, or O-alkyl phosphotriester linkages.

The DNA vectors may include nucleic acids in which modifications have been made in one or more sugar moieties and/or in one or more of the pyrimidine or purine bases. Such sugar modifications may include replacement of one or more hydroxyl groups with halogens, alkyl groups, amines, azido groups or functionalized as ethers or esters. In another embodiment, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

The DNA vector may be modified in certain embodiments with a modifier molecule such as a peptide, protein, steroid or sugar moiety. Modification of a DNA vector with such molecule may facilitate delivery to a target site of interest. In some embodiments, such modification translocates the DNA vector across a nucleus of a target cell. By way of example, a modifier may be able to bind to a specific part of the DNA vector (typically not encoding of the gene-of-interest), but also has a peptide or other modifier that has nucleus-homing effects, such as a nuclear localization signal. A non-limiting example of a modifier is a steroid-peptide nucleic acid conjugate as described by Rebuffat et al., 2002, Faseb J. 16(11):1426-8, which is incorporated herein by reference. The DNA vector may contain sequences encoding different proteins or peptides. Promoter, enhancer, stress or chemically-regulated promoters, antibiotic-sensitive or nutrient-sensitive regions, as well as therapeutic protein encoding sequences, may be included as required. Non-encoding sequences may be present as well in the DNA vector.

The nucleic acids used in the present method can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available.

In one embodiment, the DNA vector is double stranded DNA and comprises more than 700 base pairs, more than 800 base pairs or more than 900 base pairs or more than 1000 base pairs.

In another embodiment, the DNA vector is a nanoplasmid or a minicircle.

Gene editing systems can also be incorporated into delivery vehicles comprising the charged lipid. This includes a Cas9-CRISPR, TALEN and zinc finger nuclease gene editing system. In the case of Cas9-CRISPR, a guide RNA (gRNA), together with a plasmid or mRNA encoding the Cas9 protein may be incorporated into a delivery vehicle comprising the MC3-type lipid described herein. Optionally, a ribonucleoprotein complex may be incorporated into a delivery vehicle comprising the lipid described herein. Likewise, the disclosure includes embodiments in which genetic material encoding DNA binding and cleavage domains of a zinc finger nuclease or TALEN system are incorporated into a delivery vehicle together with the MC3-type lipid of the disclosure.

While a variety of nucleic acid cargo molecules are described above, it will be understood that the above examples are non-limiting and the disclosure is not to be considered limiting with respect to the particular cargo molecule encapsulated in the delivery vehicle.

For example, the MC3-type lipid described herein may also facilitate the incorporation of proteins and peptides into a delivery vehicle, which includes ribonucleoproteins. This includes both linear and non-linear peptides, proteins or ribonucleoproteins.

While pharmaceutical compositions are described above, the MC3-type lipid described herein can be a component of any nutritional, cosmetic, cleaning or foodstuff product.

Pharmaceutical Formulations

In some embodiments, the delivery vehicle comprising the cargo molecule is part of a pharmaceutical composition and is administered to treat and/or prevent a disease condition. The treatment may provide a prophylactic (preventive), ameliorative or a therapeutic benefit. The pharmaceutical composition will be administered at any suitable dosage.

In one embodiment, the pharmaceutical compositions is administered parentally, i.e., intra-arterially, intravenously, subcutaneously or intramuscularly. In yet a further embodiment, the pharmaceutical compositions are for intra-tumoral or in-utero administration. In another embodiment, the pharmaceutical compositions are administered intranasally, intravitreally, subretinally, intrathecally or via other local routes.

The pharmaceutical composition comprises pharmaceutically acceptable salts and/or excipients.

The compositions described herein may be administered to a patient. The term patient as used herein includes a human or a non-human subject.

The following examples are given for the purpose of illustration only and not by way of limitation on the scope of the invention.

EXAMPLES

Materials

The lipid 1,2-distearoyl-sn-glycero-3-phosphorylcholine (DSPC) and 1,2-dimyristoyl-rac-glycero-3-methoxypolyethylene glycol-2000 (PEG-DMG) were purchased from Avanti Polar Lipids (Alabaster, AL). Cholesterol and 10× Phosphate Buffered Saline (pH 7.4) were purchased from Sigma Aldrich (St Louis, MO). The ionizable amino-lipid was synthesized as previously described in U.S. Provisional Application No. 63/194,471 titled "Method for Producing an Ionizable Lipid", which is incorporated herein by reference.

An mRNA encoding firefly luciferase purchased from APExBIO Technology LLC (Houston, TX) was used to analyse luciferase activity.

An siRNA targeted against firefly luciferase purchased from Integrated DNA Technologies (IDT, Coralville, IA) was used to assess ability of LNP to knockdown firefly luciferase in a cell line.

Methods

Preparation of Lipid Nanoparticles (LNP) Containing mRNA or siRNA

Lipids used in the formulation, nor-MC3 or MC3, DSPC, cholesterol, and PEG-DMG, were dissolved in ethanol at the appropriate ratios to a final concentration of 10 mM total lipid. Nucleic acid (siRNA or mRNA) was dissolved in an appropriate buffer such as 25 mM sodium acetate pH 4 or sodium citrate pH 4 to a concentration necessary to achieve the appropriate amine-to-phosphate ratios. The aqueous and organic solutions were mixed using a rapid-mixing device as described in Kulkarni et al., 2018, ACS Nano, 12:4787 and Kulkarni et al., 2017, Nanoscale, 36:133347 (each incorporated herein by reference) at a flow rate ratio of 3:1 (v/v; respectively) and a total flow rate of 20 mL/min. The resultant mixture was dialyzed directly against 1000-fold volume of PBS pH 7.4. All formulations were concentrated using an Amicon centrifugal filter unit and analysed using the methods described below.

Analysis of LNP

Particle size analysis of LNPs in PBS was carried out using backscatter measurements of dynamic light scattering with a Malvern Zetasizer (Worcestershire, UK). The reported particle sizes correspond to the number-weighted average diameters (nm). Total lipid concentrations were determined by extrapolation from the cholesterol content, which was measured using the Cholesterol E-Total Cholesterol Assay (Wako Diagnostics, Richmond, VA) as per the manufacturer's recommendations. Encapsulation efficiency of the formulations was determined using the Quant-iT RiboGreen Assay kit (Invitrogen, Waltham, MA). Briefly, the total siRNA or mRNA content in solution was measured by lysing lipid nanoparticles in a solution of TE containing 2% Trioton Tx-100, and free DNA vector in solution (external to LNP) was measured based on the RiboGreen fluorescence in a TE solution without Triton. Total siRNA or mRNA content in the formulation was determined using a modified Bligh-Dyer extraction procedure. Briefly, LNP formulations containing siRNA or mRNA were dissolved in a mixture of chloroform, methanol, and PBS that results in a single phase and the absorbance at 260 nm measured using a spectrophotometer.

In Vitro Analysis in Huh7 Cells

Huh7 cells were cultured in Dulbecco's Modified Eagle Medium (DMEM) supplemented with 10% Fetal Bovine Serum (FBS). For cell treatments, 10,000 cells were added to each well in a 96-well plate. 24 hours later, the medium was aspirated and replaced with medium containing diluted LNP at the relevant concentration over a range of 0.03-10 μg/mL mRNA. Expression analysis was performed 24 hours later, and luciferase levels measured using the Steady-Glo Luciferase kit (Promega). Cells were lysed using the Glo Lysis buffer (Promega).

In Vivo Analysis in C57Bl/6 Mice

LNP-mRNA encoding firefly luciferase were injected intravenously (tail-vein) into 6-8 wk old C57BL/6 mice. Four hours following injection, the animals were euthanized and the liver and spleen and isolated. Tissue was homogenized in Glo Lysis buffer and a luciferase assay performed using the Steady Glo Luciferase assay kit (as per manufacturers recommendations).

Organic Synthesis of Nor-MC3

Unless otherwise specified, all reagents and solvents were commercial products and were used without further purification, except THF (freshly distilled from Na/benzophenone under Ar), $CH_2Cl_2$ (freshly distilled from $CaH_2$ under Ar). "Dry methanol" was freshly distilled from magnesium turnings. All reactions were performed under an argon atmosphere. Reaction mixture from aqueous workups were dried by passing over a plug of anhydrous $Na_2SO_4$ held in a filter tube and rotary-evaporated under reduced pressure. Thin-layer chromatography was performed on silica gel plates coated with silica gel (Merck 60 F254 plates) and column chromatography was performed on 230-400 mesh silica gel. Visualization of the developed chromatogram was performed by staining with $I_2$ or potassium permanganate solution. Nuclear magnetic resonance spectra, $^1H$ (300 MHz) and $^{13}C$ NMR (75 MHz), were recorded at room temperature in $CDCl_3$ solutions. $^1H$ NMR spectra were referenced to residual $CHCl_3$ (7.26 ppm) and $^{13}C$ NMR spectra were referenced to the central line of the $CDCl_3$ triplet (77.00 ppm). Chemical shifts are reported in parts per million (ppm) on the δ scale. Multiplicities are reported as "s" (singlet), "d" (doublet), "t" (triplet), "q" (quartet), "m" (multiplet), and further qualified as "app" (apparent) and "br" (broad). Low- and high-resolution mass spectra (m/z) were obtained in the electrospray (ESI) and field desorption/field ionisation (FD/FI) mode.

The synthesis of nor-MC3 from methyl linoleate was carried out as set forth below. As discussed, the synthesis of nor-MC3 involves subjecting the fatty acid ester to Claisen condensation under Mukaiyama conditions, resulting in ketoester 6 as described in Scheme 3 above. The ketoester 6 is subsequently hydrolyzed and decarboxylated to provide a ketone 7, which may be further reduced to alcohols 8 (or 8a). Esterification of alcohols 8 (or 8a) yields MC3-type lipids as set forth in co-owned and co-pending U.S. Provisional Application No. 63/194,471 (incorporated herein by reference) and described below.

(a) Synthesis of Ketoester From Methyl Linoleate: Methyl(11Z,14Z)-2-((7Z,10Z)-hexadeca-7,10-dien-1-yl)-3-oxoicosa-11,14-dienoate

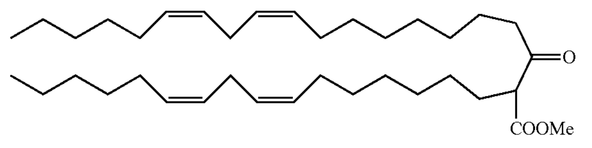

Chemical Formula: $C_{37}H_{64}O_3$
Molecular Weight: 556.92

A solution of $TiCl_4$ (9.6 g, 5.7 mL, 45.0 mmol) in toluene (12 mL) was added dropwise to a cold (0° C., ice bath), stirred solution of an appropriate methyl ester (e.g., methyl linoleate; 30.0 mmol, 8.8 g) and tributylamine ($Bu_3N$) (10.2 g, 12.9 mL, 54.0 mmol) in toluene (50.0 mL). After stirring at 0° C. for 1.5 h, the reaction was complete as determined by TLC and $^1H$ NMR. The reaction solution was then diluted with hexanes (60 mL) and water (60 mL) was cautiously added. Addition of water caused evolution of heat, so the temperature of the mixture was controlled by thorough stirring and cooling in an ice bath. The organic phase was separated and the aqueous phase was extracted with more hexane (2×40 mL). The combined organic extracts were washed with water, passed over a plug of anhydrous $Na_2SO_4$ and concentrated under vacuum. Proton NMR analysis of the residue indicated the presence of some residual toluene. Suspended inorganic matter (likely $TiO_2$) may also be present. The crude product may be purified by column chromatography (3% diethyl ether in hexanes) to afford pure ketoester (96%) but may be advanced directly to the next step. NMR indicated that the product existed as a mixture of keto (major) and enol derivatives, typically in a 2:1 ratio. $^1H$ NMR (keto form) δ 5.37 (m, 8H), 3.77 (s, 3H), 3.45 (t, 1H), 2.79 (t, 4H), 2.40 (t, 2H), 2.07 (m, 8H), 1.85-1.20 (m, 32H), 0.91 (t, 6H). $^{13}C$ NMR (keto form) δ 205.6, 170.6, 130.2, 130.1, 129.9, 129.8, 59.2, 52.4, 42.0, 32.1, 29.9, 29.8, 29.8, 29.7, 29.5, 29.4, 29.4, 29.3, 29.2, 29.1, 28.4, 27.6, 27.4, 27.3, 27.3, 23.6, 22.8, 14.3 (some peaks are doubled). LRMS: m/z 557 $[M+H]^+$, 579 $[M+Na]^+$ (b) Hydrolysis and Decarboxylation of the Ketoester to Produce the Ketone: (6Z,9Z,26Z,29Z)-Pentatriaconta-6,9,26,29-tetraen-18-one

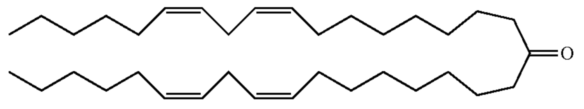

Chemical Formula: $C_{35}H_{62}O$
Molecular Weight: 498.88

Aqueous 10% w/vol NaOH (5 mL) was added to a solution of the above crude ketoester (5.0 g) in 95% ethanol (25 mL). The mixture was stirred at room temperature overnight. The reaction was checked for completion by adding 3-4 drops of the reaction mixture to 3N aqueous HCl solution (0.5 mL), extracting the mixture with hexanes, evaporating the combined extracts to dryness, and checking the residue by $^1H$ NMR. The disappearance of the $OCH_3$ signal and a downfield shift of the triplet at 3.45 (ketoester) to 3.51 (ketoacid) indicated that the reaction was complete. The reaction mixture was concentrated on a rotary evaporator to remove ethanol. The aqueous residue was cooled in an ice bath, diluted with hexanes (60 mL), and vigorously stirred during careful dropwise addition of conc. aqueous HCl solution (heat evolved). When the mixture attained pH~1, the phases were separated and the aqueous layer was extracted with more hexanes (2×20 mL). The combined organic extracts were washed with DI water (30 mL), passed over a plug of anhydrous $Na_2SO_4$, and concentrated on the rotary evaporator. An NMR spectrum of the crude product was recorded to ascertain the presence of the desired ketoacid. The flask containing the residue from the rotary evaporation was capped with a septum and thoroughly purged with argon (balloon; needle vent). The flask was heated with a heat gun (while still sealed under argon and vented with a needle) until uncomfortably hot to the touch (100-130° C.), whereupon decarboxylation started. Bubbling of the residue was noticeable as the decarboxylation reaction proceeded. After approximately 10 min, no further bubbling was evident. The flask was cooled to room temperature and the residue was again analyzed by $^1H$ NMR, which revealed it to be nearly pure ketone. If desired, the crude ketone may be purified by column chromatography (gradient 1→3% v/v ether in hexanes; 97% yield). The crude ketone, however, is most advantageously introduced directly to the next steps. $^1H$ NMR δ 5.32 (m, 8H), 2.74 (t, 4H), 2.35 (t, 4H), 2.02 (m, 8H), 1.55-1.20 (m, 28H), 0.87 (t, 6H). $^{13}C$ NMR δ 210.9, 130.0, 129.8, 128.0, 127.8, 42.6, 31.4, 29.5, 29.24, 29.22, 29.1, 29.0, 27.0 (2 overlapping peaks), 25.5, 23.7, 22.5, 14.0. LRMS m/z 499 $[M+H]^+$, 521 $[M+Na]^+$.

(c) Reduction of the Ketone to an Alcohol: (6Z,9Z,26Z,29Z)-Pentatriaconta-6,9,26,29-tetraen-18-ol

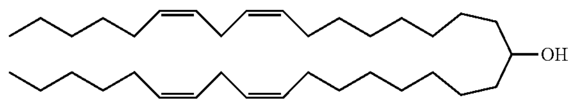

Chemical Formula: $C_{35}H_{64}O$
Molecular Weight: 500.90

Solid $NaBH_4$ (2 mmol) was added portion-wise to a stirred solution of ketone (2 mmol) in 95% ethanol (10 mL) at 0° C. (ice bath). After stirring at 0° C. for 1 h, the reaction was checked for completion, either by TCL (5% ether in hexanes) or, more reliably, by adding 3-4 drops of the reaction mixture to saturated aqueous $NH_4Cl$ solution (0.5 mL), extracting with hexanes, evaporating the combined extracts to dryness, and checking the residue by $^1H$ NMR. Either method indicated that the reaction was complete. The reaction was quenched by careful addition of aqueous saturated $NH_4Cl$ solution (caution should be taken due to $H_2$ evolution and foaming) and concentrated on the rotary evaporator to remove the ethanol. The aqueous residue was extracted with hexanes (3×10 mL). The combined extracts were passed through a plug of anhydrous $Na_2SO_4$ and concentrated to afford crude alcohol, which was purified by silica gel column chromatography with 5→10% v/v ethyl acetate in hexanes (91% yield). $^1H$ NMR δ 5.36 (m, 8H), 3.58 (m, 1H), 2.78 (t, 4H), 2.1-1.9 (m, 8H), 1.6-1.2 (m, 36H), 0.89 (t, 6H). LRMS: m/z 501 $[M+H]^+$, 523 $[M+Na]^+$ (d) Procedure for Esterification of the Alcohol (4-dimethylamino)butanoylation to Produce (6Z,9Z,26Z,29Z)-Pentatriaconta-6,9,26,29-tetraen-18-yl 4-(dimethylamino)butanoate (=nor-MC3)

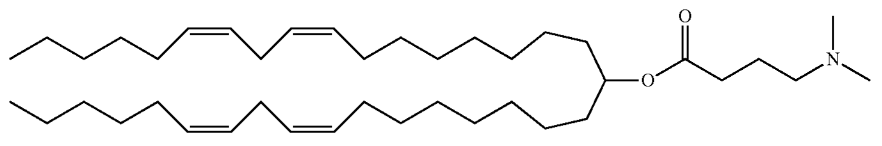

Chemical Formula: $C_{41}H_{75}NO_2$
Molecular Weight: 614.06

A solution of the above alcohol (1 mmol, 1.0 equiv), 4-dimethylaminobutyric acid hydrochloride (1.2 mmol, 1.2 equiv), diisopropylethylamine (1.5 mmol, 1.5 equiv), and DMAP (0.1 mmol, 0.1 equiv) in dry $CH_2Cl_2$ (3 mL) was stirred at room temperature for 5 minutes prior to the addition of EDCI (1.5 mmol, 1.5 equiv). The mixture was stirred overnight at room temperature, under argon, whereupon TLC (5% MeOH in $CH_2Cl_2$) and $^1H$ NMR indicated that the reaction had completed. The solution was diluted with more $CH_2Cl_2$ (10 mL) and sequentially washed with aqueous saturated $NaHCO_3$ (5 mL) and water (10 mL). The organic phase was passed over a plug of anhydrous $Na_2SO_4$ and concentrated in vacuo. The residue of crude product was purified by flash column chromatography with 3% v/v MeOH in $CH_2Cl_2$, containing 0.1% $NEt_3$ (78% yield). $^1H$ NMR δ 5.33 (m, 8H), 4.85 (m, 1H), 2.75 (t, 4H), 2.40 (m, 2H), 2.34 (t, 2H), 2.20 (s, 6H), 2.02 (m, 8H), 1.77 (m, 2H), 1.50 (m, 6H), 1.39-1.17 (m, 36H), 0.87 (t, 6H). $^{13}C$ NMR δ 173.3, 130.1, 130.0, 127.9, 127.8, 74.1, 59.0, 45.4, 34.1, 32.4, 31.5, 29.7, 29.6, 29.5, 29.4, 29.33, 29.30, 29.2, 27.15, 27.14, 25.3, 23.1, 14.8. LRMS: m/z 614 $[M+H]^+$.

Example 1: MRNA-Containing LNPs Comprising Nor-MC3 Ionizable Lipid Exhibit Transfection Efficiencies That are Superior to the MC3 Benchmark LNP formulations containing the ionizable lipids, nor-MC3 or MC3, DSPC, cholesterol, and PEG-DMG were prepared containing mRNA encoding luciferase. The lipid nanoparticles comprise 50/10/38.5/1.5 mol % of ionizable lipid/DSPC/chol/PEG-DMG and the nitrogen-to-phosphorus ratio (N/P) was 6.

Figure 1B:
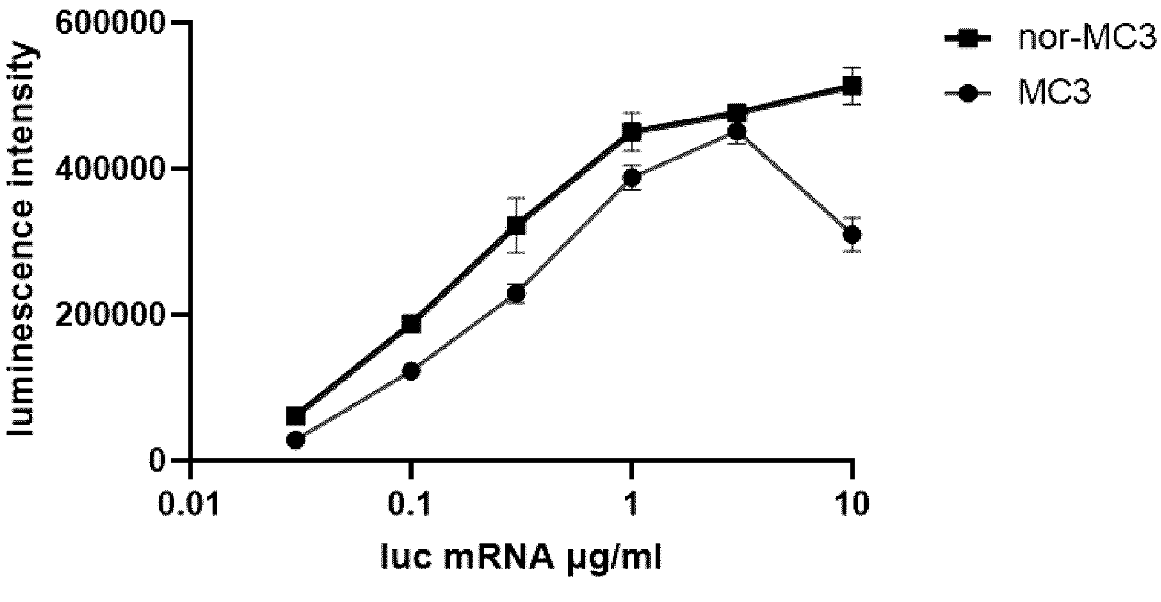
FIG. 1B shows luminescence intensity as a function of mRNA concentration after addition of the mRNA-containing LNPs comprising the ionizable lipid nor-MC3 or MC3 to HuH7 cells. The LNPs are composed of 50/10/38.5/1.5 mol % of ionizable lipid/DSPC/chol/PEG-DMG (N/P=6) and the mRNA encodes firefly luciferase.

Transfection efficiencies of the LNPs comprising nor-MC3 verses the MC3 benchmark ionizable lipid are shown in FIG. 1B. The transfection efficiency of LNPs comprising nor-MC3 was superior to that of the MC3 benchmark lipid at each concentration of mRNA measured (μg/mL mRNA) after addition to Huh7 and significantly improved at the highest dose measured (10 μg/mL mRNA). These results are particularly surprising since MC3 is a state-of-the-art ionizable lipid for LNP formulations encapsulating nucleic acid and its carbon chains are unsaturated $C_{18}$ moieties derived from linoleic acid, which are reported to be the best chains yet identified for maximum efficacy of siRNA formulations. (Semple et al., 2010, Nat. Biotechnol. 28:172-176 and Heyes et al., 2005, J. Controlled Release, 107:276-287). Accordingly, shorter chain lipids would be expected to have reduced potency, yet the opposite effect was observed.

The results of characterization studies of LNP size, PDI and encapsulation efficiency of mRNA LNPs containing nor-MC3 and MC3 are shown in FIG. 1A. Advantageously, the mRNA-LNP containing nor-MC3 lipid exhibited similar size, PDI and encapsulation efficiency (entrapment) of the mRNA as the mRNA-LNP containing MC3.

Example 2: MRNA-Containing LNPs Comprising Nor-MC3 Exhibit In Vivo Delivery of the mRNA to Liver and Spleen that is Superior to the MC3 Benchmark LNP formulations containing 50/10/38.5/1.5 mol % of nor-MC3 or MC3 ionizable lipid/DSPC/chol/PEG-DMG and mRNA encoding luciferase were tested for in vivo biodistribution in the liver and spleen after injection to C57BL/6 mice. The mRNA dose was 1 mg/kg. Luminescence intensity in the liver or spleen was measured at 4 hours post-injection.

Figure 1C:
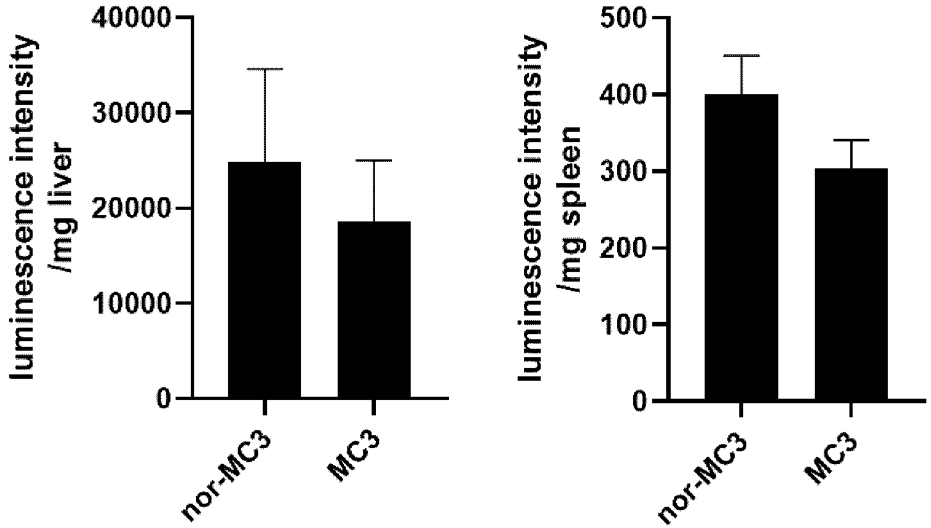
FIG. 1C shows luminescence intensity/mg in the liver (left graph) or spleen (right graph) for the mRNA-containing LNPs comprising the ionizable lipid nor-MC3 or MC3 after 4 hours post-intravenous administration to C57Bl/6J mice. The LNPs contain 50/10/38.5/1.5 mol % of ionizable lipid/DSPC/chol/PEG-DMG (N/P=6).

The results shown in FIG. 1C show that luminescence intensity per mg liver was higher for nor-MC3 than the MC3 benchmark. Similar results were found for luminescence intensity per mg spleen.

The results showing superior delivery of mRNA to not only the liver, but also the spleen with nor-MC3-LNPs, are particularly surprising as MC3 having C18 unsaturated carbon chains (derived from linoleic acid) would be expected to provide improved efficacy for nucleic acid delivery relative to the shorter chain nor-MC3 having $C_{17}$ unsaturated chains.

Example 3: SiRNA-Containing LNPs Containing Nor-MC3 Exhibit Transfection Efficiencies that are Comparable to the MC3 Benchmark As demonstrated in Example 1 and Example 2, mRNA encapsulating LNP formulations with nor-MC3 have superior or comparable transfection efficiency and significant improvements in biodistribution in vivo relative to MC3 formulations. In vitro physical characterization and transfection studies comparing nor-MC3 to MC3 were also conducted with LNPs containing siRNA. The results are discussed below.

LNP formulations containing the ionizable lipids, nor-MC3 or MC3, DSPC, cholesterol, and PEG-DMG were prepared containing siRNA encoding luciferase as described above. The lipid nanoparticles comprise 50/10/38.5/1.5 mol % of ionizable lipid/DSPC/chol/PEG-DMG and the nitrogen-to-phosphorus ratio (N/P) was 3.

Figure 2A:
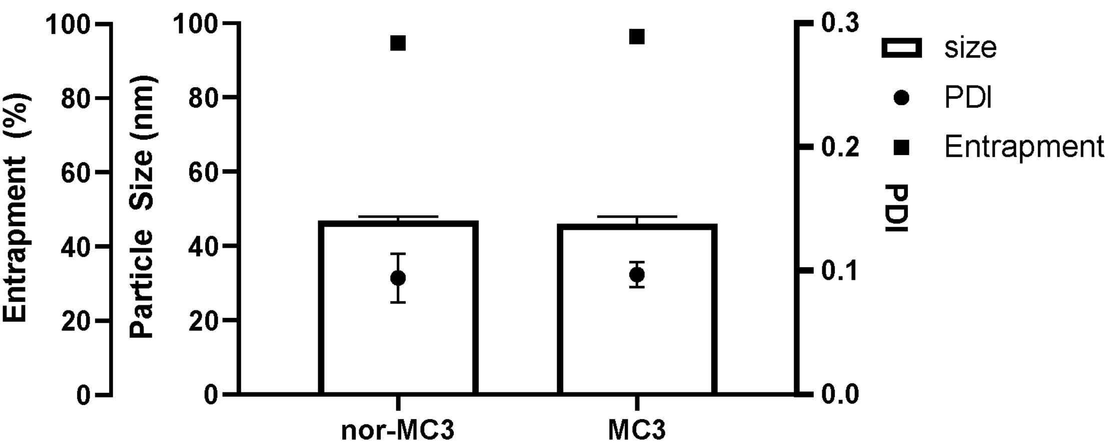
FIG. 2A is a bar graph showing entrapment (%), particle size and PDI of siRNA-containing LNPs comprising the ionizable lipid nor-MC3 or MC3. The LNPs contain 50/10/38.5/1.5 mol % of ionizable lipid/DSPC/chol/PEG-DMG and the N/P was 3.
Figure 2B:
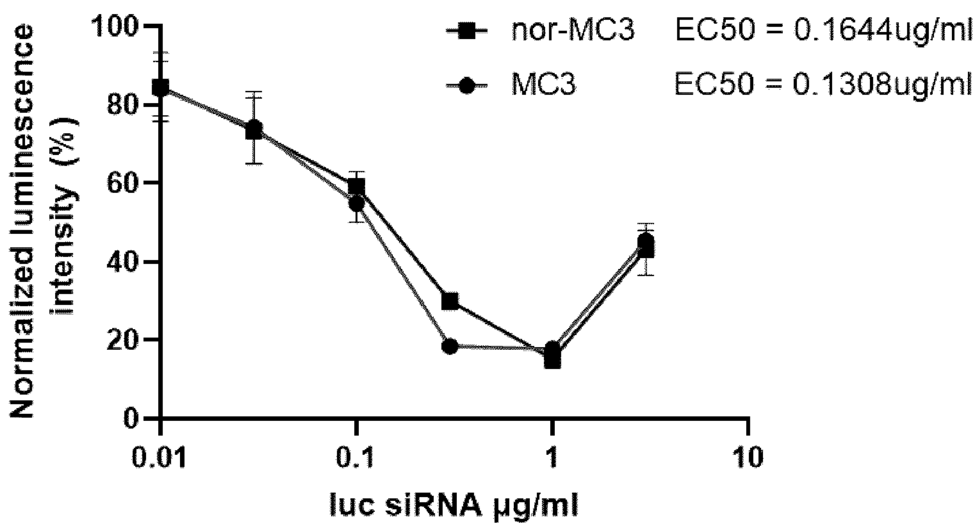
FIG. 2B shows normalized luminescence intensity (%) after addition of siRNA-containing LNPs comprising the ionizable lipid nor-MC3 or MC3 to 22Rv1 cells modified to stably express luciferase. The LNPs contain 50/10/38.5/1.5 mol % of ionizable lipid/DSPC/chol/PEG-DMG (N/P=3) and the siRNA encodes luciferase.

Transfection efficiency is shown in FIG. 2B. The transfection efficiency of siRNA LNPs containing nor-MC3 was generally comparable to that of the MC3 benchmark lipid, but was better than MC3 at 0.5 μg/mL siRNA. The half maximal effective siRNA concentration ($EC_{50}$) for LNP formulations of nor-MC3 and MC3 were relatively comparable (nor-MC3 $EC_{50}$=0.1644 and MC3 $EC_{50}$=0.1308 μg/mL siRNA). These results are also surprising since nor-MC3 would be expected to have lower potency in an in vitro transfection than MC3 in view of previous studies reporting that $C_{18}$ moieties derived from linoleic acid provide the highest potency for siRNA delivery.

The results of nor-MC3 vs. MC3 on LNP size, PDI and encapsulation efficiency of siRNA are shown in FIG. 2A. Advantageously, the LNP comprising nor-MC3 lipid exhibited similar size, PDI and encapsulation efficiency (entrapment) of the siRNA as MC3.

The examples are intended to illustrate the preparation of short-chain MC3-type lipids, formulations and properties thereof but are in no way intended to limit the scope of the invention.

The invention claimed is:

1. A lipid having a structure of nor-MC3:

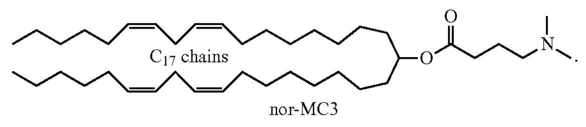 [SMILES: CCCCC/C=C\C/C=C\CCCCCCCC(CCCCCCC/C=C\C/C=C\CCCCC)OC(=O)CCCN(C)C]

nor-MC3

2. A drug delivery vehicle comprising the lipid of claim 1.

3. The drug delivery vehicle of claim 2, wherein the drug delivery vehicle is a lipid nanoparticle.

4. The drug delivery vehicle of claim 3, wherein the drug delivery vehicle comprises a helper lipid and a hydrophilic polymer-lipid conjugate.

5. The drug delivery vehicle of claim 4, wherein the helper lipid is a sterol, a diacylglycerol, a ceramide or derivatives thereof.

6. The drug delivery vehicle of claim 5, wherein the diacylglycerol is selected from dipalmitoylphosphatidylcholine, distearoylphosphatidylcholine, dioleoylphosphatidylethanolamine, palmitoyloleoyl-phosphatidylcholine, palmitoyloleoyl-phosphatidylethanolamine, palmitoyloleoyl-phosphatidylglycerol, dipalmitoyl-phosphatidylethanolamine, dimyristoyl-phosphatidylethanolamine, distearoyl-phosphatidylethanolamine, monomethyl-phosphatidylethanolamine, dimethyl-phosphatidylethanolamine, dielaidoyl-phosphatidylethanolamine, stearoyloleoyl-phosphatidylethanolamine, egg phosphatidylcholine and mixtures thereof.

7. The drug delivery vehicle of claim 2, wherein the drug delivery vehicle comprises a nucleic acid.

8. The drug delivery vehicle of claim 7, wherein the nucleic acid is RNA selected from siRNA, snRNA, miRNA and mRNA.

9. The drug delivery vehicle of claim 7, wherein the nucleic acid is a single stranded antisense oligonucleotide.

10. The drug delivery vehicle of claim 7, wherein the nucleic acid is DNA.

11. A method of producing the nor-MC3 lipid of claim 1 comprising:

(i) reacting methyl linoleate in a Claisen condensation reaction in the presence of a catalyst to produce a ketoester of the formula methyl (11Z,14Z)-2-((7Z,10Z)-hexadeca-7,10-dien-1-yl)-3-oxoicosa-11,14-dienoate;

(ii) reacting the ketoester via a hydrolysis and decarboxylation to produce a ketone of the formula (6Z,9Z,26Z,29Z)-Pentatriaconta-6,9,26,29-tetraen-18-one;

(iii) reducing the ketone to produce an alcohol having the formula (6Z,9Z,26Z,29Z)-Pentatriaconta-6,9,26,29-tetraen-18-ol; and (iv) preparing the nor-MC3 lipid from the alcohol thereof by esterifying the alcohol with 4-(Dimethylamino) butyric acid, thereby producing the nor-MC3 lipid.

* * * * *